(12) United States Patent
Pond et al.

(10) Patent No.: US 8,671,994 B2
(45) Date of Patent: Mar. 18, 2014

(54) SYRINGE FILLING APPARATUS

(75) Inventors: Gary J. Pond, Racine, WI (US); Dennis Cotic, Oconomowoc, WI (US)

(73) Assignee: Inter-Med, Inc., Racine, WI (US)

( * ) Notice: Subject to any disclaimer, the term of this patent is extended or adjusted under 35 U.S.C. 154(b) by 16 days.

(21) Appl. No.: 12/387,195

(22) Filed: Apr. 29, 2009

(65) Prior Publication Data

US 2010/0059140 A1 Mar. 11, 2010

Related U.S. Application Data

(63) Continuation-in-part of application No. 12/231,790, filed on Sep. 5, 2008.

(51) Int. Cl.
*B65B 1/04* (2006.01)
*B67C 3/00* (2006.01)
*B65B 3/04* (2006.01)

(52) U.S. Cl.
USPC ............. 141/27; 141/320; 141/322; 141/330; 141/351; 141/363

(58) Field of Classification Search
USPC ............ 141/27, 320, 322, 330, 351, 363–366
See application file for complete search history.

(56) References Cited

U.S. PATENT DOCUMENTS

| 4,253,501 | A | * | 3/1981 | Ogle ............................... 141/27 |
|---|---|---|---|---|
| 4,312,349 | A | * | 1/1982 | Cohen ........................... 604/406 |
| 5,222,530 | A | * | 6/1993 | Baker et al. ...................... 141/18 |
| 5,566,729 | A | * | 10/1996 | Grabenkort et al. ............ 141/25 |
| 6,425,420 | B2 | * | 7/2002 | Both et al. ......................... 141/2 |
| 6,820,662 | B2 | * | 11/2004 | Crawford et al. ............. 141/319 |
| 7,418,981 | B2 | * | 9/2008 | Baker et al. ....................... 141/9 |
| 2004/0154690 | A1 | * | 8/2004 | Osborne et al. ................. 141/27 |
| 2006/0025747 | A1 | * | 2/2006 | Sullivan et al. ............... 604/411 |

* cited by examiner

*Primary Examiner* — Ryan Reis
(74) *Attorney, Agent, or Firm* — Ryan Kromholz & Manion, S.C.

(57) ABSTRACT

A syringe filling apparatus having a housing, a fluid reservoir, and a port for providing a fluid pathway between the syringe and the fluid reservoir. The apparatus has an alarm to indicate the fluid level within the reservoir. The apparatus has a heating system for heating the fluid within the reservoir to a predetermined temperature.

8 Claims, 6 Drawing Sheets

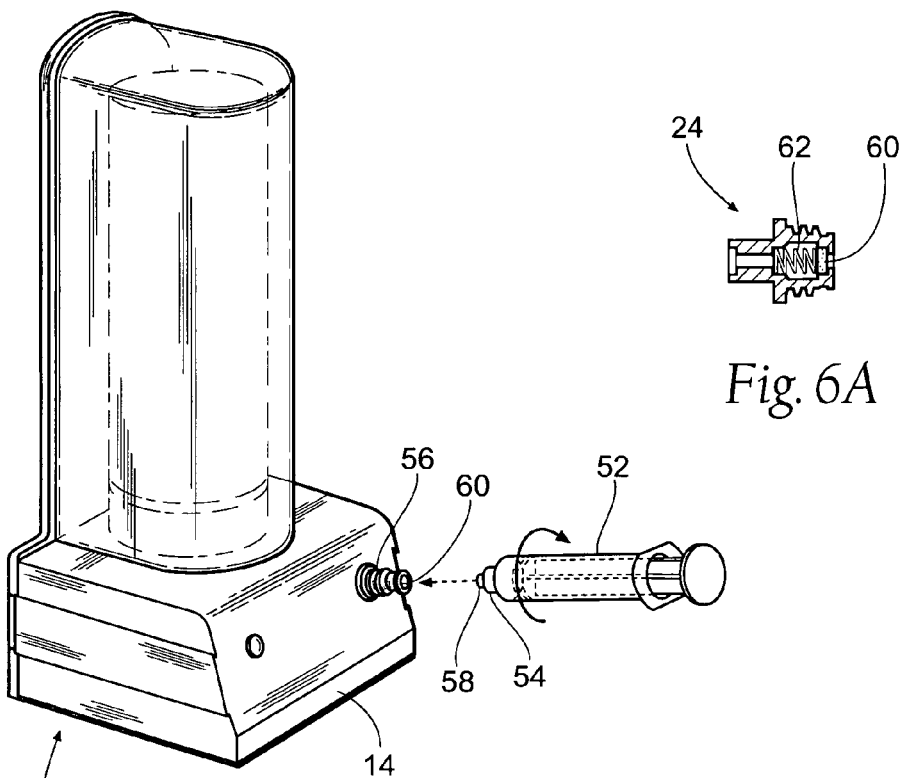
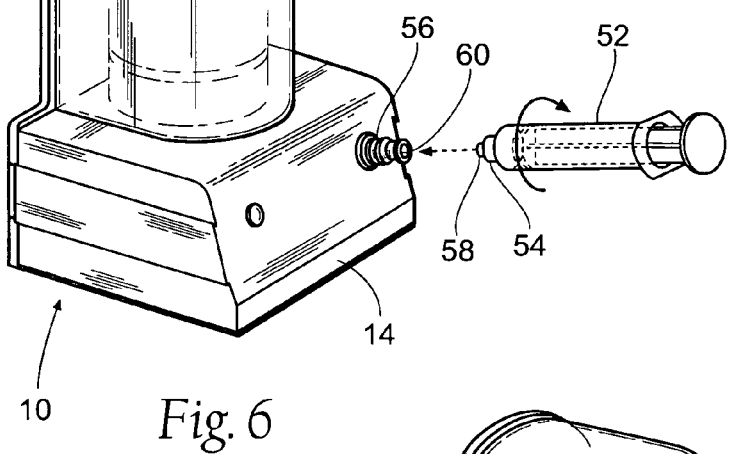
Fig. 6
Fig. 6A
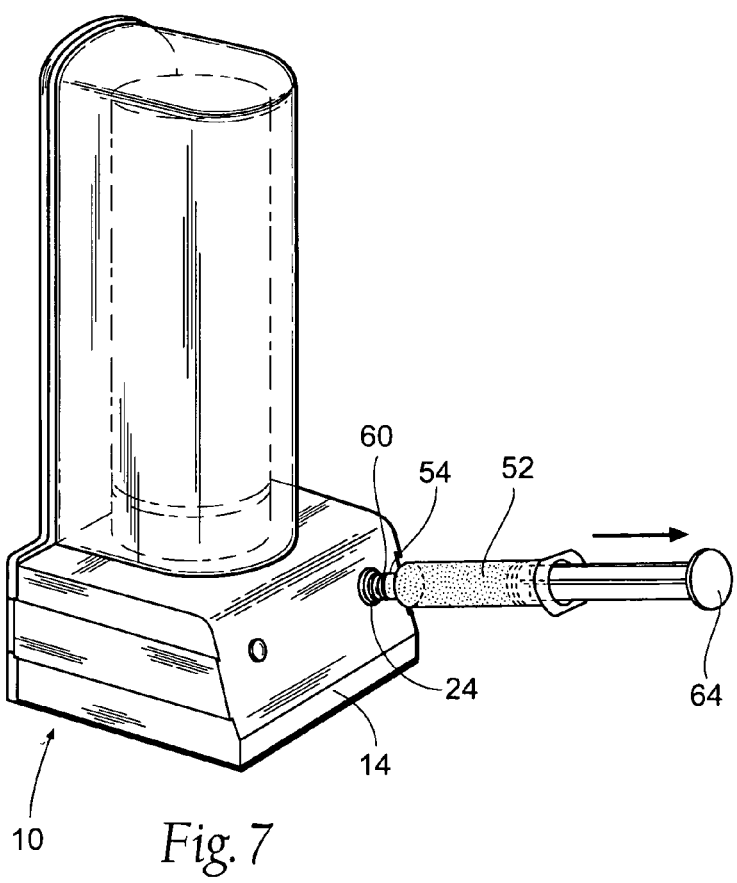
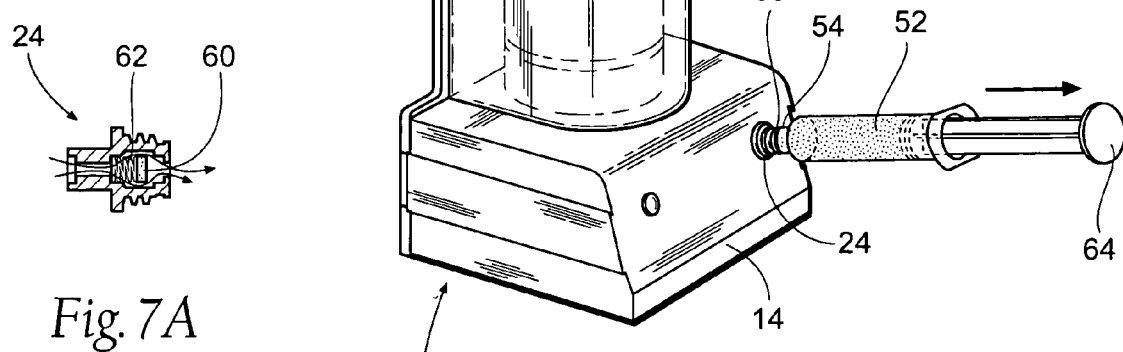
Fig. 7A
Fig. 7

SYRINGE FILLING APPARATUS

RELATED APPLICATIONS

The present application is a continuation-in-part of co-pending application, U.S. Ser. No. 12/231,790, filed on 5 Sep. 2008.

BACKGROUND OF THE INVENTION

The present invention relates to dental and medical devices for delivering fluids and, more specifically, to devices for filling individual devices for fluid delivery.

When delivering fluids for use in dental or medical situations, care is generally taken so that a precise amount of fluid is used and delivered during a procedure, whether the fluid is a medicine, an antiseptic, water, or other fluid. Devices, such as syringes, are metered so that an accurate amount of fluid will be delivered and/or an accurate amount of fluid will be introduced into the syringe.

Unless a syringe is prepackaged with a specific fluid, the specific fluid is usually stored in a container that holds much more fluid than is needed for an individual dose or syringe, with the fluid being transferred to the syringe from the container. Care must be taken when filling the syringe, to minimize the amount of fluid that may spill when filling the syringe and to make sure that the syringe is precisely filled. Care must also be taken to insure that the larger container of fluid is not contaminated when fluid is transferred from the larger container to the syringe.

SUMMARY OF THE INVENTION

The present invention provides an apparatus for filling individual syringes from a reservoir of fluid that may incorporate a larger container of fluid. The device generally comprises a housing, a reservoir, and a port connected to the reservoir, which is designed to receive a syringe or similar device. The reservoir preferably is connected to a fluid container, as well. The port provides a fluid tight seal that prevents fluid from exiting the port, unless connected to the syringe.

The present invention is arranged to minimize potential contamination of the fluid within the reservoir and/or the container connected to the reservoir before the fluid is transferred to the syringe.

The present invention also provides an arrangement to alert the user when a predetermined amount of fluid is left in the reservoir, so that a user may refill the reservoir, or replace the fluid container that is fed into the reservoir, as desired.

The present invention further provides a heating system so that fluid within the apparatus can be heated prior to filling the syringe with fluid.

BRIEF DESCRIPTION OF THE DRAWINGS

FIG. 6 is a perspective view of a filling apparatus according to the present invention arranged to receive a syringe.

FIG. 6A is a cross-sectional view of a port used in the present invention, with the port being in a closed position to prevent the flow of fluid through the port.

FIG. 7 is a perspective view of a syringe being coupled to the filling apparatus of FIG. 6.

FIG. 7A is a cross-sectional view of the port of FIG. 6A, with the port being in an open position to allow the flow of fluid through the port.

DESCRIPTION OF THE PREFERRED EMBODIMENT

Although the disclosure hereof is detailed and exact to enable those skilled in the art to practice the invention, the physical embodiments herein disclosed merely exemplify the invention which may be embodied in other specific structures. While the preferred embodiment has been described, the details may be changed without departing from the invention, which is defined by the claims.

Figure 1:
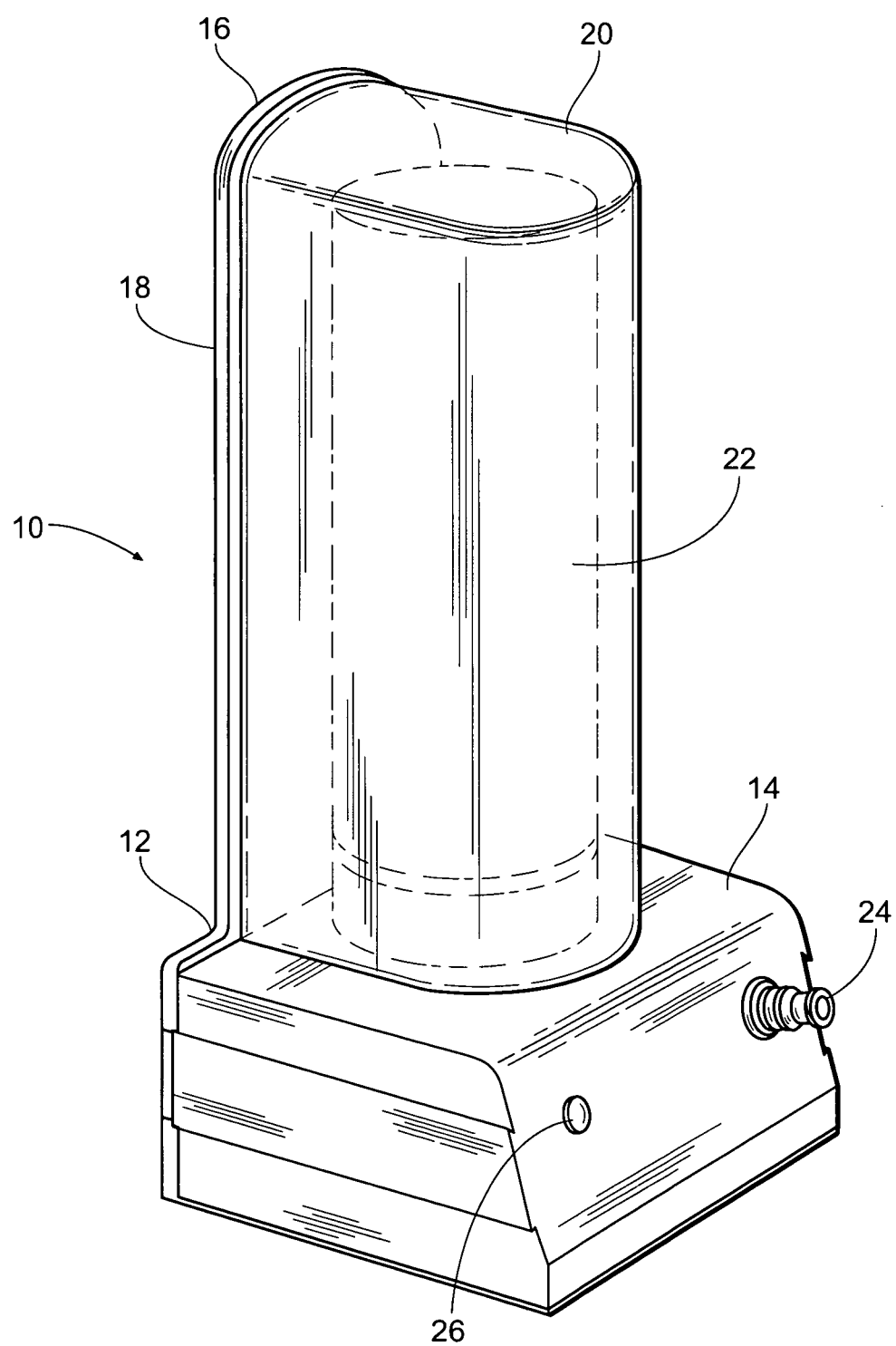
FIG. 1 provides a perspective view of a filling apparatus according to the present invention.

FIG. 1 depicts a perspective view of a syringe filling apparatus 10 in accordance with the present invention. The apparatus generally comprises a housing 12, which comprises a base section 14 and an upright section 16. The upright section 16 comprises a backing section 18 and a front section 20, which enclose a fluid container 22. The base section 14 supports a port 24, which will be discussed in more detail with respect to FIGS. 6-9. The base section 14 also supports a signal 26 that will alert a user when the fluid container 22 may need to be replaced. The signal 26 will be described further with respect to FIGS. 8 and 9.

Figure 2:
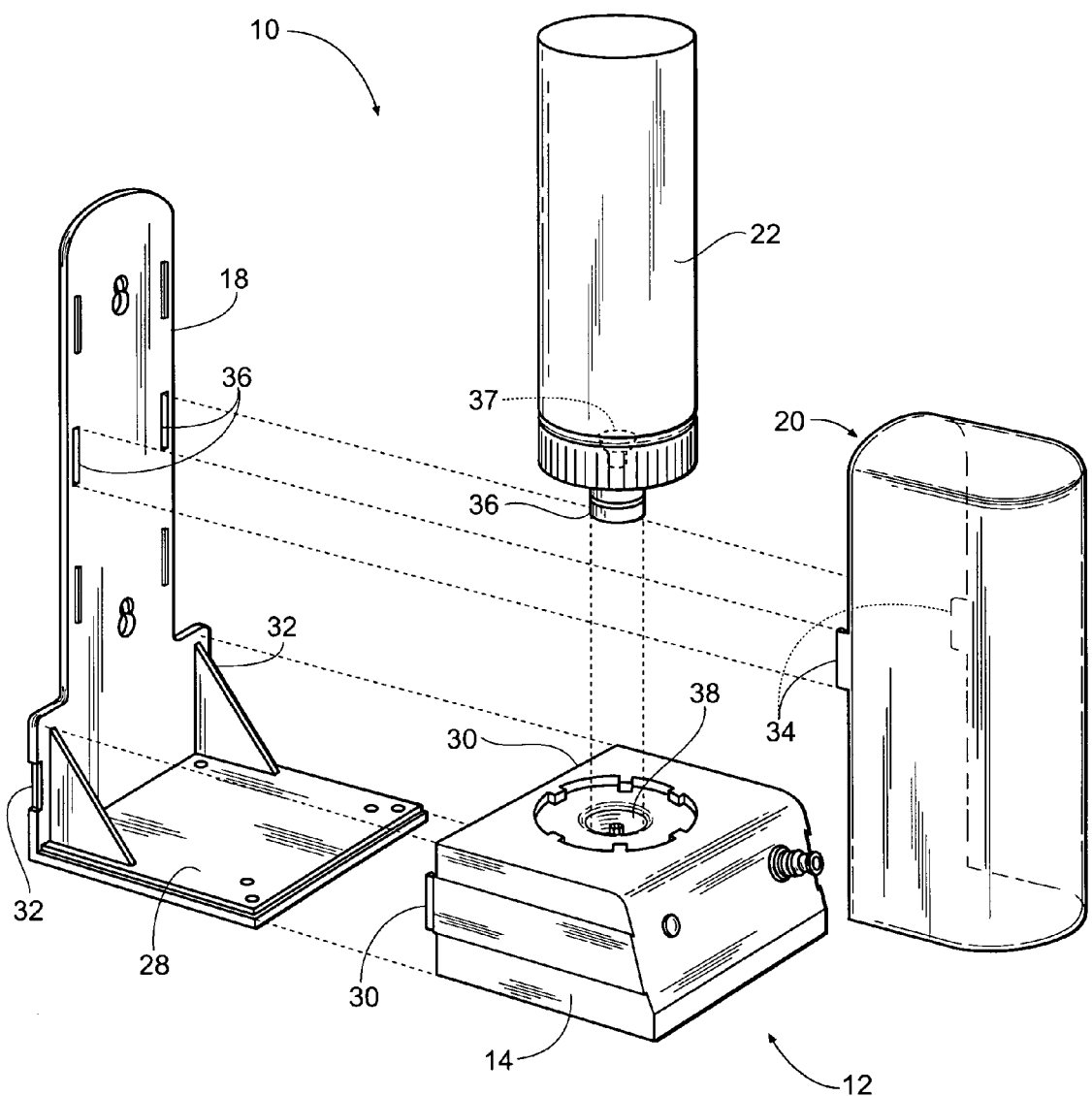
FIG. 2 is an exploded view of the housing of the apparatus depicted in FIG. 1.

FIG. 2 provides an exploded view of the housing 12 of the apparatus 10. The backing section 18 has a bottom portion 28 that is arranged to slidingly mate with the base section 14, with base section 14 resting upon the bottom portion 28. The base section 14 has a pair of posts 30 that will mate with a pair of slots 32 located on the backing section 18 to secure the base section 14 and the backing section 18 to one another. The backing section 18 also mates with the front section 20 to form an enclosure for the fluid container 22. The front section 20 also has a pair of posts 34 that mates with slots 36 located on the backing section 18. The front section 20 could be designed to be pivotally connected to the backing section 18, to allow for easy opening and closing of the housing 12, when necessary, to remove or replace the container 22. Alternatively, locks, clasps, or other securing means could be used to further close the housing 12. Thus, the front section 20, the backing section 18, and the base section 14 form the housing 12 that provides protection for the container 22 in a manner that is easy to assemble. It is understood that the housing could comprise different arrangements, sizes, or sections, and still fall within the scope of the present invention.

Still referring to FIG. 2, the fluid container 22 has an opening 36 that will be arranged to allow fluid to flow from the container 22 to a reservoir 38 located within the base section 14, with the container 22 preferably being removably secured to or within the reservoir 38 in a fluid tight arrangement. A movable plug 37 (shown in phantom) is located within the opening 36. The container 22 and the reservoir 38 will be discussed further with respect to FIGS. 3-5. It should be understood that the reservoir 38 could be designed so that it is may be filled with fluid directly, and it is not necessary to use a container 22 or containers 22. However, the use of the container 22 coupled or connected to the reservoir minimizes spills and contamination associated with transferring fluid from the container 22 to the reservoir 38, or from the container 22 directly to a syringe. It is understood that any of these arrangements would fall within the scope of the present invention.

Figure 3:
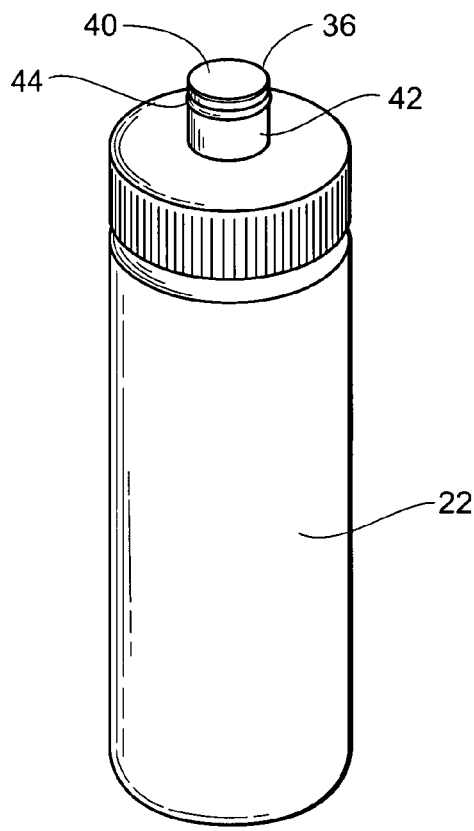
FIG. 3 provides a perspective view of a fluid container that can be used in conjunction with the present invention.

FIG. 3 provides a perspective view of the container 22 used in the present invention, with the container 22 preferably being a standard size used in the industry. The opening 36 of the container 22, which is also preferably of a typical dimension used within the industry, normally will be sealed prior to use, preferably being hermetically sealed, with a foil-type seal 40 commonly used for sealing containers. The container 22 has a neck 42 that supports an O-ring 44, which assists the container 22 in being fluidly connected to the reservoir 38 (FIGS. 2 and 4) in a fluid-tight manner. It should be understood that other sealing means beside the O-ring 44 could be used to provide a seal between the container 22 and the reservoir 38, such as a press fit or threaded arrangement.

Figure 4:
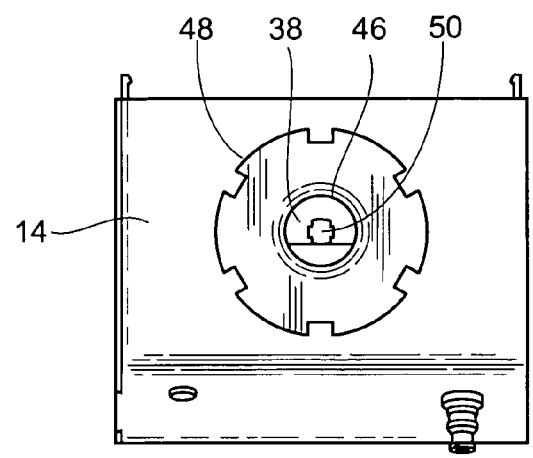
FIG. 4 is an overhead plan view of a base section of the housing depicted in FIG. 2.
Figure 5:
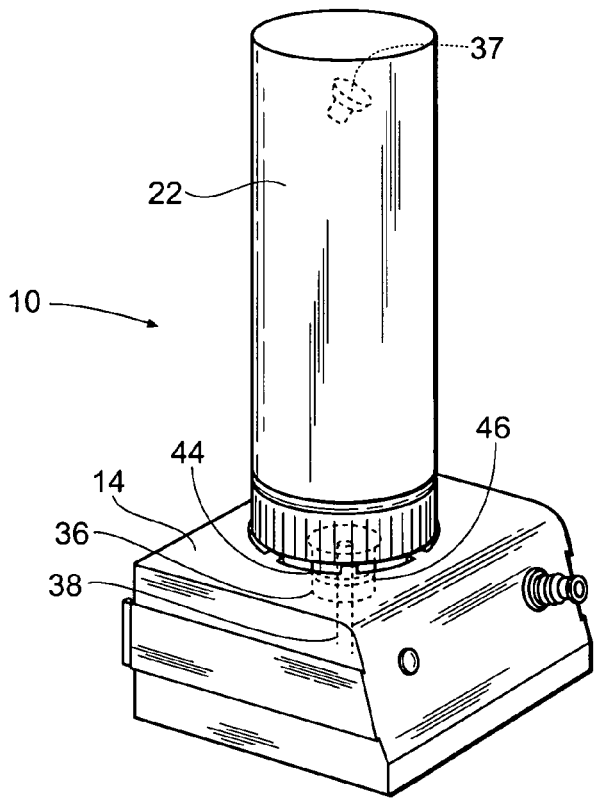
FIG. 5 is a perspective view of the container of FIG. 3 and the base of FIG. 4 connected to one another.

FIG. 4 shows an overhead view of the base section 14, which houses the reservoir 38. The reservoir has a perimeter 46, which is substantially the same size as the opening 36 of the container 22. The base section 14 further has an edge 48 that will support the container 22 when the container 22 is mated with the reservoir 38. If desired, the edge 48 could be of a size that allows the container 22 to be placed inwardly of the edge 48, thereby providing further support for the container 22, when the container is in the dispensing position, as shown in FIG. 5. A post 50 is located within the reservoir 38, with the post 50 being designed to pierce the seal 40 located on the opening 36 of the container 22 when the container 22 is mated with the reservoir 38. The arrangement further minimizes potential spilling or possible contamination of the fluid. It should be understood the shape and design of the reservoir 38 and the base section 14 could be changed and still fall within the scope of the present invention.

Referring to FIG. 5, the container 22 is shown coupled with the reservoir 38, which is shown in phantom. The opening 36 is inserted into the reservoir 38, with the O-ring 44 being sealingly fit within the perimeter 46 to form a fluid tight arrangement between the container 22 and the reservoir 38. Also, as the opening 36 is inserted into the reservoir 38, the post 50 pierces the seal 40, thereby allowing fluid to pass from the container 22 into the reservoir 38 in a fluid-tight manner. The plug 37 (shown in phantom) is pushed out of the opening by the post 50, and will float upwardly, as the plug 37 is preferably lighter, or less dense, than the fluid within the container 22. Thus, fluid can be transferred from the container 22 to the reservoir 38 without spilling any fluid when opening the container 22.

FIGS. 6 and 7 demonstrate a syringe 52 being filled from the apparatus 10. The syringe 52 mates with the port 24 located on the base section 14. The syringe 52 preferably has a LUER-LOK® arrangement, typically known and used in the industry, with a threaded end section 54 that will mate with a threaded section 56 located on the port 24. The syringe 52 typically has a fluid passageway 58 that extends outwardly past the threaded end section 54, which allows the passageway 58 to contact the port 24 prior to the threaded end section 54 contacting the port 24. The port 24 has a movable plug 60, which is normally biased outwardly in a first position when there is no external force on the plug 60, as shown in FIG. 6A. A spring 62 or other similar biasing means can be used to keep the plug 60 in a closed position, which will prevent fluid from passing through the port 24 until desired. That is, the arrangement of the port 24 and the plug 60 prevents fluid from flowing through the port 24 until an external device, such as the syringe 52 is attached to or mated with the port 24.

Referring particularly to FIG. 7, the syringe 52 is shown coupled or mated with the port 24. The threaded end section 54 is threaded onto the threaded section 56 of the port 24, which cause the passageway 58 to make contact with the plug 60, thereby inwardly biasing the plug 60 in a second position against the spring 62, as shown in FIG. 7A. Fluid can then pass through the port 24, and outwardly into the syringe 52. When a plunger 64 is pulled backwardly, fluid passes through the passageway 58 and into the syringe 52. Once a desired amount of fluid is added to the syringe 52, the threaded end section 54 will be unthreaded from the port 24. The spring 62 biases the plug 60 outwardly and seals the port 24, easily and efficiently, with minimal fluid leakage or loss. Thus, the plug 60 moves easily between an open position that prevents the flow of fluid to a closed position that allows the flow of fluid, without fluid leakage.

Figure 8:
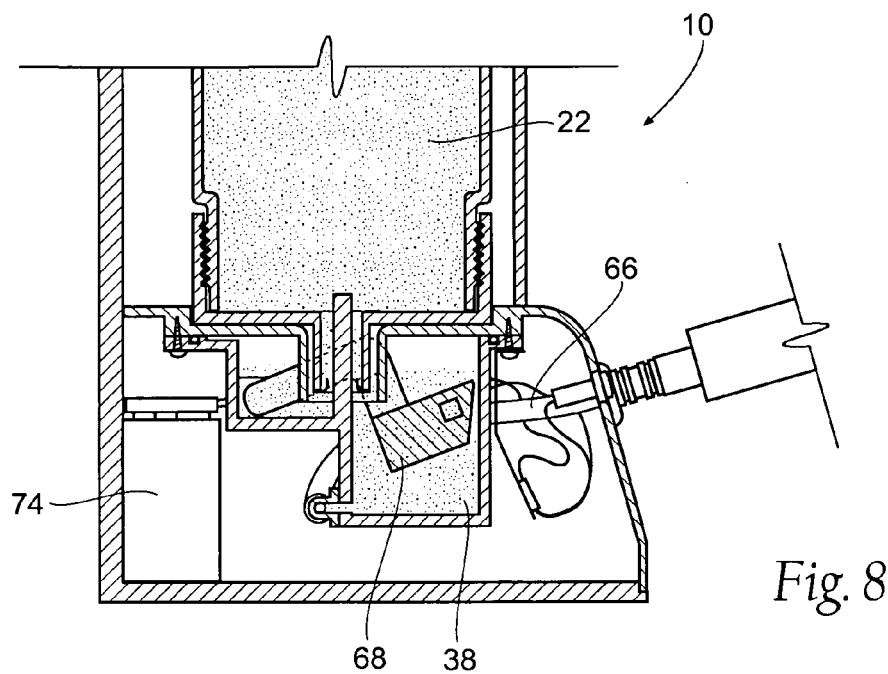
FIG. 8 is a partial cut-away cross-sectional view of a reservoir of the present filling apparatus containing fluid.
Figure 9:
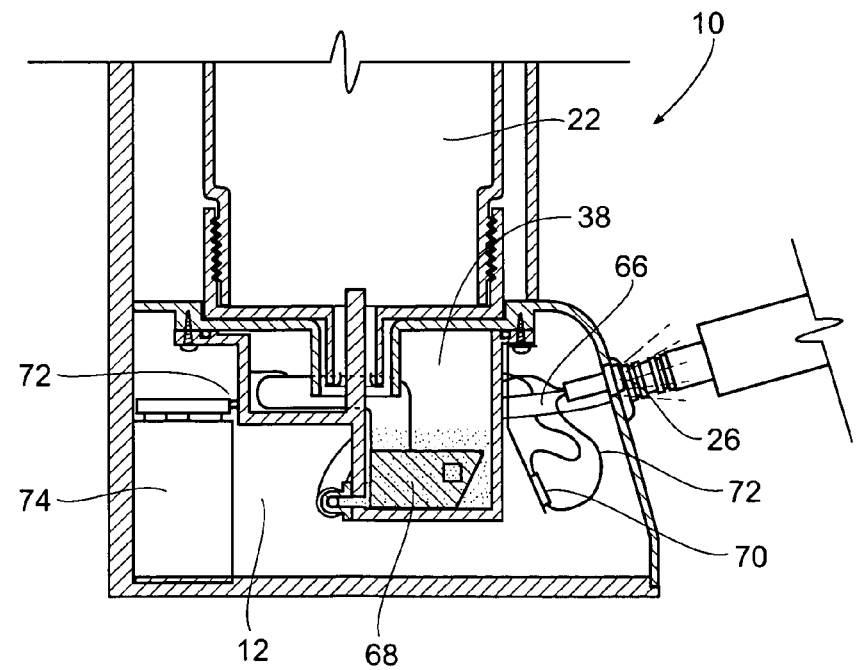
FIG. 9 is a partial cut-away cross-sectional view of the reservoir of FIG. 8, having less fluid within the reservoir.

FIGS. 8 and 9 provide a cross-sectional view of the apparatus 10, the container 22, and the reservoir 38. The reservoir 38 is preferably located below the container 22, so that the container 22 will drain completely into the reservoir 38. A fluid conduit 66 connects the reservoir 38 to the port 24. A float 68 is located within the reservoir 38. In FIG. 8, the float 68 is shown floating within the fluid in the reservoir 38. In FIG. 9, fluid has been extracted from the container 22 and the reservoir 38, thereby allowing the float 68 to move down towards the bottom of the reservoir 38. When this happens, the alarm 26 will be triggered, thereby telling the user that the container 22 should be replaced and/or the reservoir 38 should be refilled with fluid. The alarm is preferably a visual or audible alarm. In a preferred arrangement, the alarm 26 is triggered by the use of a reed switch 70. The reed switch 70 is connected in a circuit by wires 72 to the alarm 26 and a power source, such as a standard 9-volt battery 74. Once the float 68, which is preferably made of a magnetizable material, comes sufficiently close to the reed switch 70, the circuit will be closed, thereby activating the alarm 26, indicating that the fluid source should be replaced or replenished. As shown in FIG. 9, the alarm 26 is activated, demonstrated by the alarm 26 visually lighting up.

The apparatus 10 provides for an efficient system for filling individual syringes from a larger container or reservoir without worrying about spilling the fluid during the transferring process and, also, minimizing contamination of the fluid. Likewise, the apparatus 10 provides for an alarm or warning system to notify the operator that the reservoir and/or container are out of fluid. Preferably, as shown in FIG. 9, the alarm 26 will notify the user of fluid depletion before the reservoir 38 is completely empty, thereby preventing any potential disruption in the syringe filling process.

Figure 10:
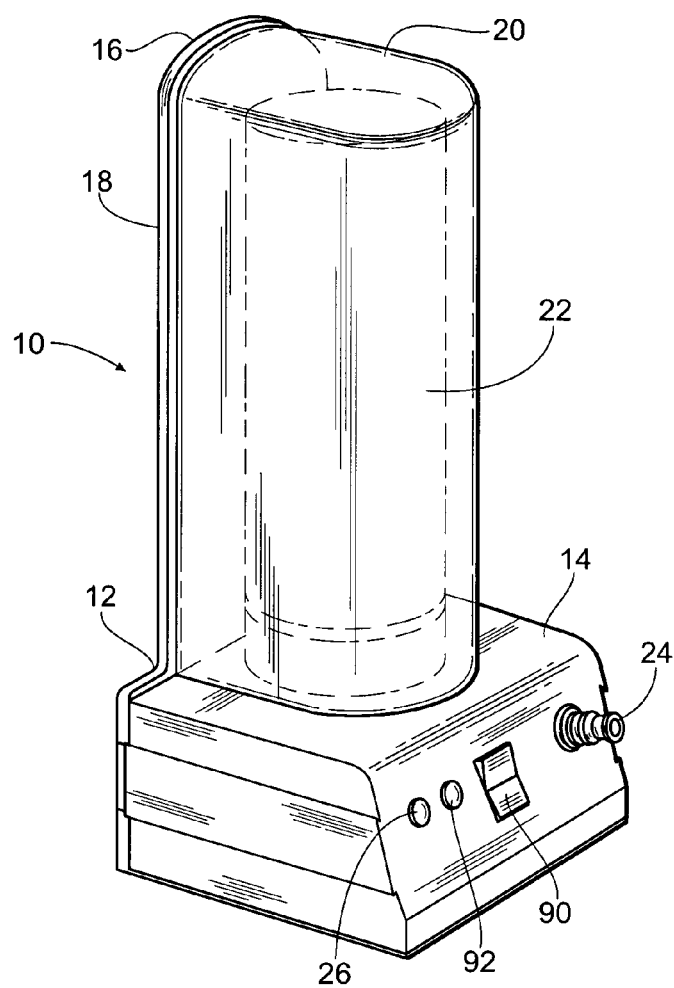
FIG. 10 is a perspective view of the present invention, incorporating a heating control switch into the housing of the device.

The apparatus 10 in FIG. 10 further includes an on/off switch 90. The switch 90 is connected to a heating system, which allows the fluid within the apparatus 10 to be heated prior to filling a syringe 52 (FIG. 7) with fluid. Heating the fluids in the apparatus may allow for increased medicinal reaction rates and increased medicinal antimicrobial activity for the fluids A secondary indicator 92 may alert the user when the heater system is turned on and heating fluid in the reservoir.

Figure 11:
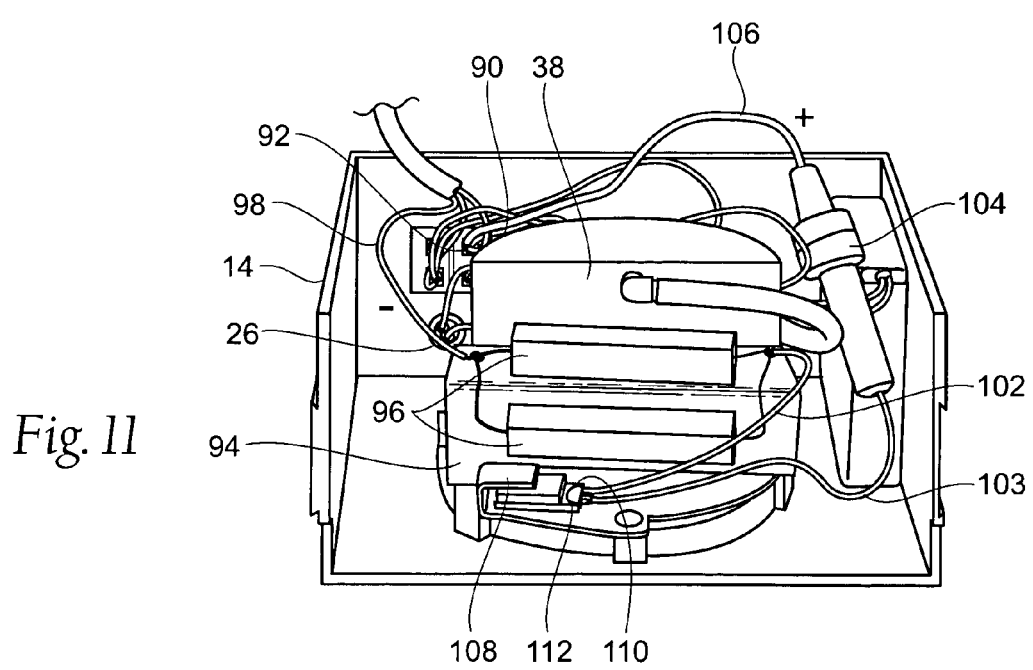
FIG. 11 is a perspective, partially cut-away, inverted view of the base section, demonstrating the heating system for the present invention.

FIG. 11 provides an inverted view of the base section 14. A metal bracket heat sink 94 is shown supporting a pair of resistor heaters 96, which forms a portion of the heating system. The resistors 96 are connected in parallel. In simplistic terms, by applying an electrical current between wires 98 and 102, the resistors heat up and provide heat energy to the metal bracket heat sink 94, which in turn hearts up the solution reservoir 38. To regulate the electrical current and heat energy to the resistor heaters 96, a temperature switches 108 and fuse holder 104 are added in series with the positive power supply wire lead 106. When the switch 90 is turned on, an electrical current goes through the wire 106, fuse holder 104, temperature switch 108, input terminal 112, through temperature switch 108, output terminal 110, and into heater resistors 96. The heater resistors 98 continue to heat up until a set temperature point is reached at which time the temperature switch 108 opens the electric circuit connections at input terminal 112 and output terminal 110, stopping the heating process. As the heat temperature starts to decrease, the temperature switch 108 senses the temperature reduction and therefore closes the electrical circuit, starting the heating process all over again. By automatically switching on and off the temperature, the switch 108 maintains a predetermined temperature set point. For protection, the fuse holder 104 has an internal fuse, not shown, to protect the electronic heating circuit. The switch 108 will pass energy, i.e. heat, to the bracket 94, which in turn will pass heat to the reservoir 38, thereby heating the fluid within the reservoir. The energy passing through the system preferably is sufficient enough to heat the fluid within the reservoir 38, but will not damage the reservoir 38, which is preferably designed from a plastic or thermoplastic material. As stated, the resistor heaters 96 are connected in parallel, but series arrangements or more or fewer resistors are possible. In one arrangement, the two resistors are both 10 ohm (Ω) resistors arranged in parallel.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention, which is defined by the claims.

We claim:

1. An apparatus for filling a syringe with fluid, said apparatus comprising:
    a fluid container having a container opening;
    a housing;
    a fluid reservoir located within said housing, said fluid reservoir comprising a post extending therein to be received by said container opening;
    said fluid reservoir having a reservoir opening arranged to directly and matingly receive said container opening in a fluid tight manner;
    said housing further comprising a port comprising an opening in fluid communication with said reservoir, said port being arranged to directly matingly receive said syringe in a fluid tight manner; and
    sealing means comprising a plug located within said opening of said port for sealing said port, said sealing means selectively allowing fluid to flow from said reservoir to said syringe, said plug capable of moving from a first normally biased, non-mated position within said opening of said port to a second mated position when said syringe and said port are directly mated with one another, said plug preventing fluid from flowing out of said port in said first non-mated position, said sealing means allowing fluid to pass through said port in said second mated position;
    means for indicating a predetermined fluid level within said reservoir; and
    means for determining the fluid level within said reservoir, said means for determining the fluid level located at least substantially within said reservoir;
    whereby said plug being capable of moving back to said first non-mated position when said syringe removed from said port.

2. The apparatus according to claim 1, wherein said indicating means comprises a visual indicator, said indicator being illuminated when said predetermined fluid level is reached.

3. An apparatus for filling a syringe with fluid from a container having an opening, said apparatus comprising:
    a housing;
    a fluid reservoir located within said housing, said reservoir comprising an opening for receiving said opening of said container;
    a port in fluid communication with said reservoir, said port being arranged to threadingly and directly mate with said syringe;
    sealing means comprising a plug located within said port for sealing said port, said plug selectively allowing fluid to flow from said reservoir to said syringe;
    means for indicating a predetermined fluid level within said reservoir;
    means for determining the fluid level within said reservoir, said means for determining the fluid level located at least substantially within said reservoir; and
    means for heating said fluid in said reservoir to a predetermined temperature.

4. The apparatus according to claim 3, further comprising a power source connected to said indicating means.

5. The apparatus according to claim 4, further comprising an electrical circuit connected to said power source and said indicating means.

6. The apparatus according to claim 3, further comprising means for normally biasing said sealing means against said port.

7. The apparatus according to claim 1 further comprising:
    means for heating the fluid within the reservoir to a predetermined temperature.

8. The apparatus according to claim 7 further comprising means for indicating when said fluid is heated to a predetermined temperature.

* * * * *